(12) United States Patent
Nitta

(10) Patent No.: US 9,400,251 B2
(45) Date of Patent: Jul. 26, 2016

(54) FINE PARTICLE MEASURING APPARATUS

(71) Applicant: Sony Corporation, Tokyo (JP)

(72) Inventor: Nao Nitta, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/717,197

(22) Filed: May 20, 2015

(65) Prior Publication Data

US 2015/0253247 A1 Sep. 10, 2015

Related U.S. Application Data

(63) Continuation of application No. 14/289,214, filed on May 28, 2014, now Pat. No. 9,068,946, which is a continuation of application No. 13/605,256, filed on Sep. 6, 2012, now Pat. No. 8,816,311.

(30) Foreign Application Priority Data

Sep. 13, 2011 (JP) ................. 2011-199892

(51) Int. Cl.
| | |
|---|---|
| *G01N 23/04* | (2006.01) |
| *G01N 21/64* | (2006.01) |
| *G01N 15/14* | (2006.01) |
| *G01N 21/27* | (2006.01) |
| *G01N 15/10* | (2006.01) |
| *G01N 15/00* | (2006.01) |

(52) U.S. Cl.
CPC ........ *G01N 21/6486* (2013.01); *G01N 15/1429* (2013.01); *G01N 15/1434* (2013.01); *G01N 15/1459* (2013.01); *G01N 21/274* (2013.01); *G01N 21/64* (2013.01); *G01N 21/645* (2013.01); *G01N 2015/0065* (2013.01); *G01N 2015/1006* (2013.01); *G01N 2021/6417* (2013.01); *G01N 2201/06113* (2013.01)

(58) Field of Classification Search
CPC .............. G01N 21/64; G01N 21/6486; G01N 2015/1006
See application file for complete search history.

(56) References Cited

U.S. PATENT DOCUMENTS

| | | | |
|---|---|---|---|
| 5,117,466 A | 5/1992 | Buican et al. | |
| 5,126,581 A | 6/1992 | Furuya et al. | |

(Continued)

FOREIGN PATENT DOCUMENTS

| | | |
|---|---|---|
| JP | S60162942 | 8/1985 |
| JP | 61-173141 | 8/1986 |

(Continued)

OTHER PUBLICATIONS

M.R. Gauci et al., "Observation of Single-Cell Fluorescence Spectra in Laser Flow Cytometry," Cytometry, vol. 25, pp. 388-393, 1996. (6 pages).

(Continued)

*Primary Examiner* — Kiho Kim
(74) *Attorney, Agent, or Firm* — K&L Gates LLP

(57) ABSTRACT

A fine particle measuring apparatus is provided. The fine particle measuring apparatus includes a detection unit configured to detect light emitted from a fine particle and a processing unit having a memory device storing instructions which when executed by the processing unit, cause the processing unit to calculate a corrected intensity value of the detected light and generate spectrum data based on the corrected intensity value.

17 Claims, 12 Drawing Sheets

(56) References Cited

U.S. PATENT DOCUMENTS

| | | |
|---|---|---|
| 5,367,474 A | 11/1994 | Auer et al. |
| 5,426,499 A | 6/1995 | Kosaka et al. |
| 5,619,324 A | 4/1997 | Harvill et al. |
| 5,861,951 A | 1/1999 | Uesugi et al. |
| 5,880,833 A | 3/1999 | Iwasaki |
| 6,139,800 A | 10/2000 | Chandler |
| 7,280,204 B2 | 10/2007 | Robinson et al. |
| 2009/0108214 A1 | 4/2009 | Shinoda et al. |
| 2010/0256943 A1 | 10/2010 | Donnenberg et al. |
| 2012/0208263 A1 | 8/2012 | Fish |

FOREIGN PATENT DOCUMENTS

| | | | | |
|---|---|---|---|---|
| JP | 04-65654 | 3/1992 | | |
| JP | H06186156 | 7/1994 | | |
| JP | H10132660 | 5/1998 | | |
| JP | 11108929 A | * 4/1999 | ........... | G01N 33/543 |
| JP | 2000205952 | 7/2000 | | |
| JP | 2003-083894 | 3/2003 | | |
| JP | 2003083894 | 3/2003 | | |
| JP | 2009109218 | 5/2009 | | |
| JP | 2013508718 | 3/2013 | | |
| WO | 2011048539 | 4/2011 | | |

OTHER PUBLICATIONS

Office Action issued in Japanese Application 2014226991 mailed Aug. 4, 2015 (10 pages).

Office Action issued in Chinese Application 201210326660.X mailed Nov. 4, 2015 16 pages).

Office Action issued in JP Application 2014226991 mailed Jan. 19, 2016 (12 pages).

* cited by examiner

WAVELENGTH [nm]

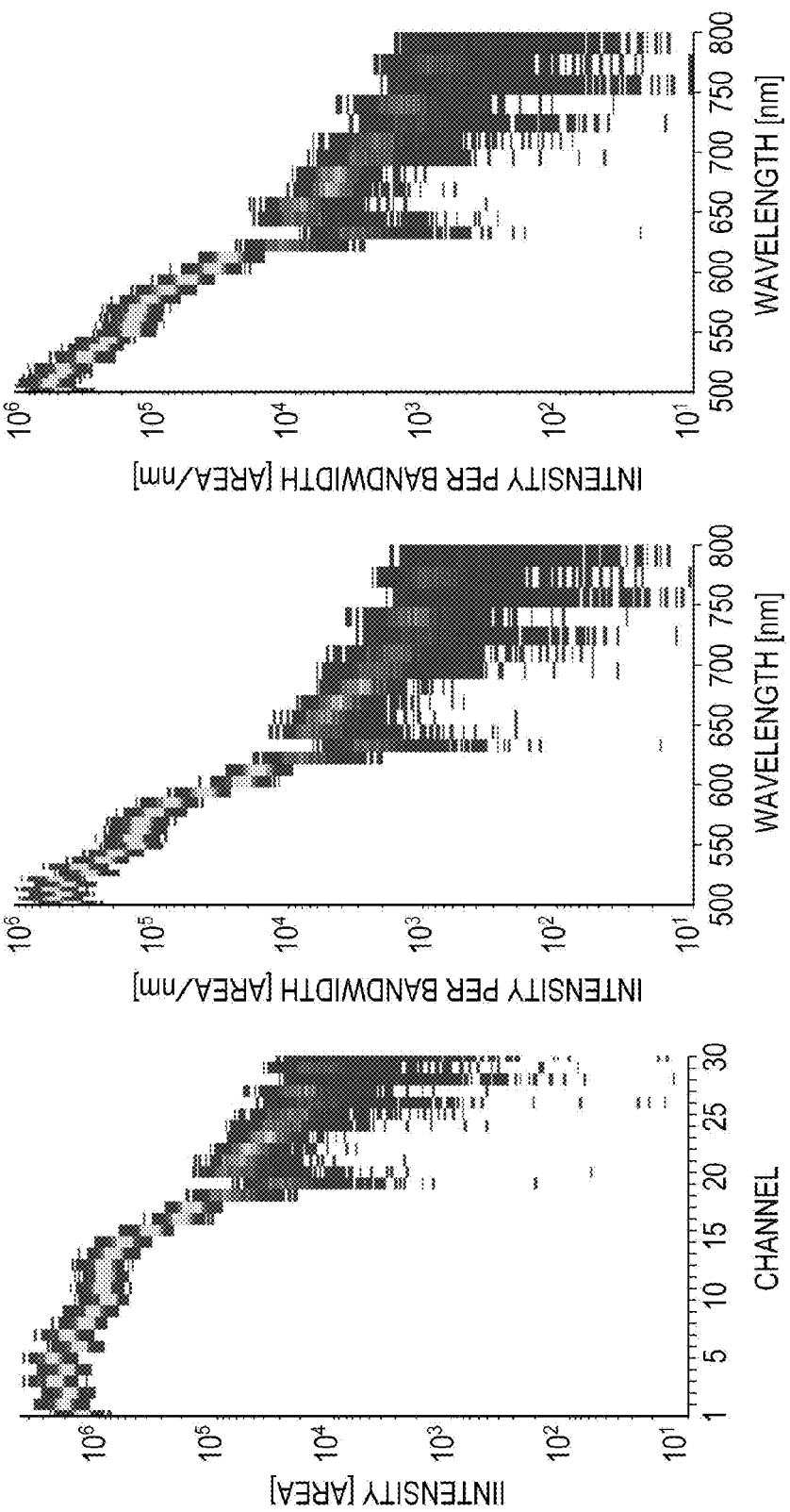

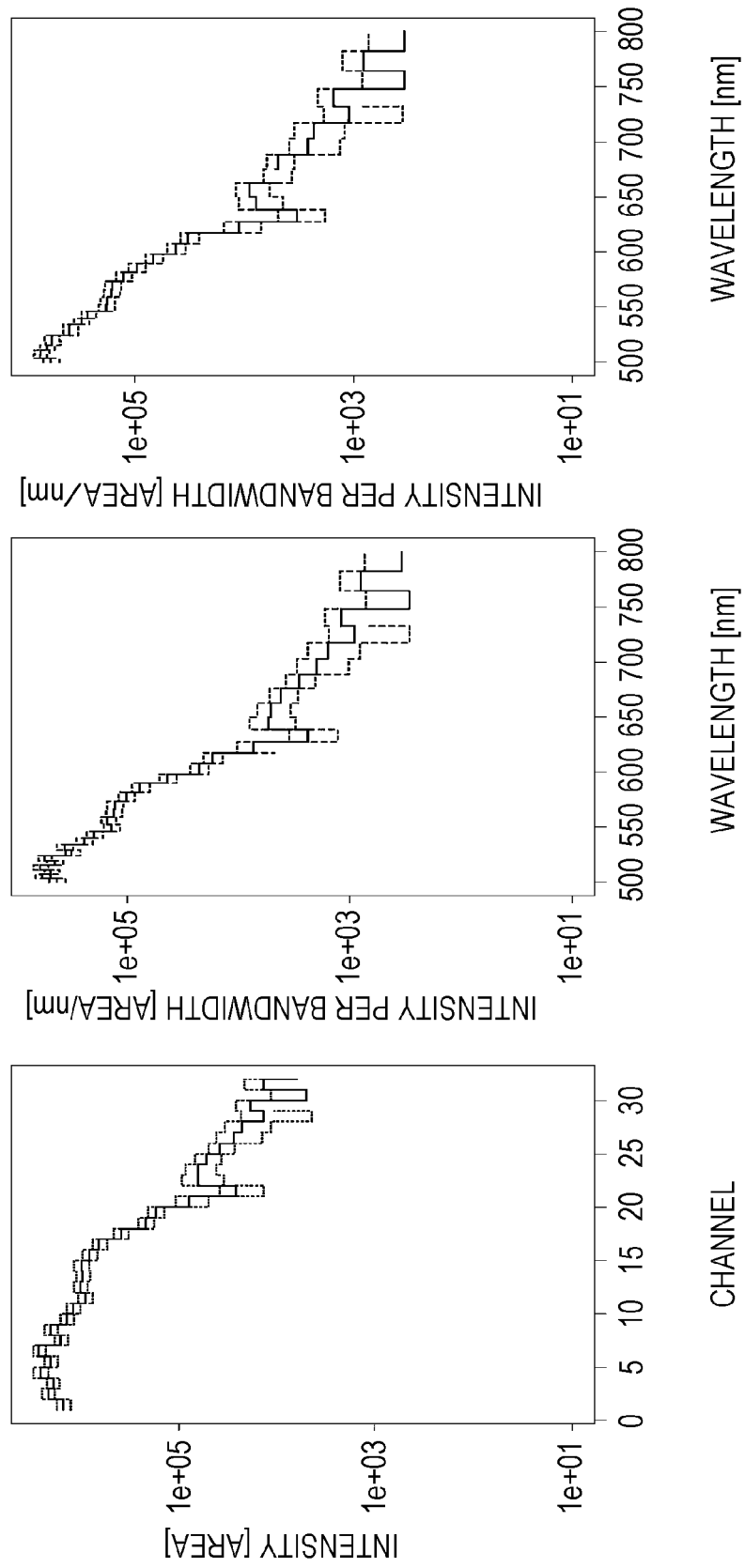

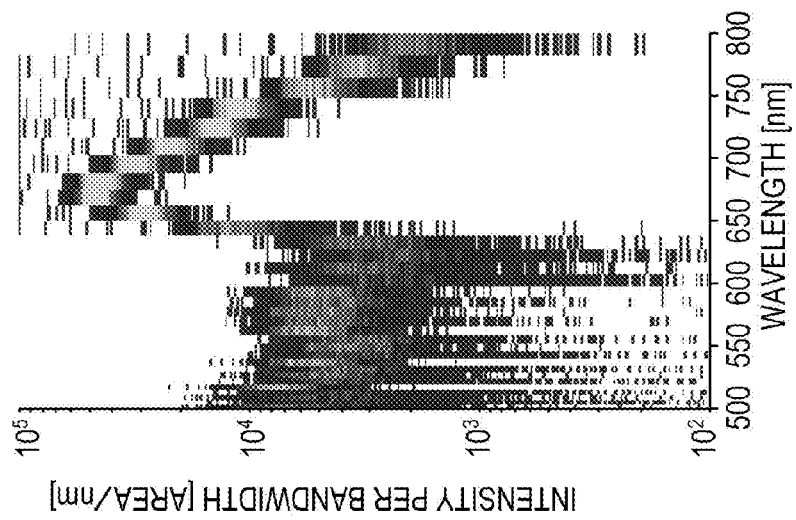
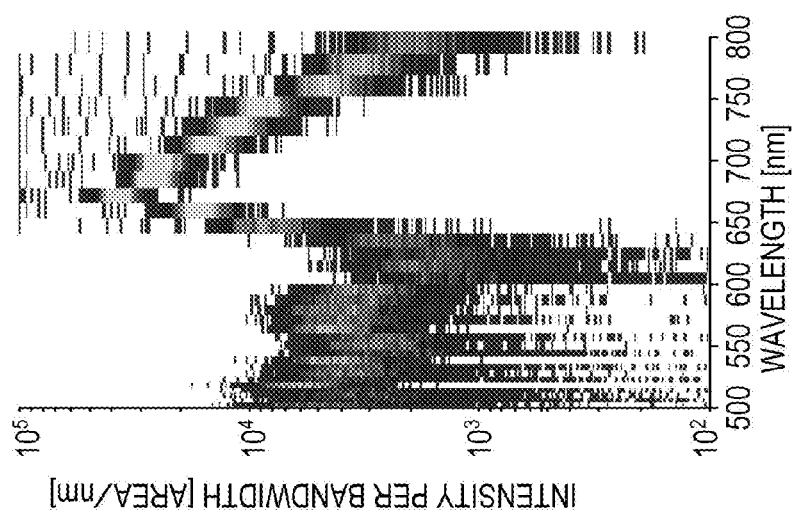
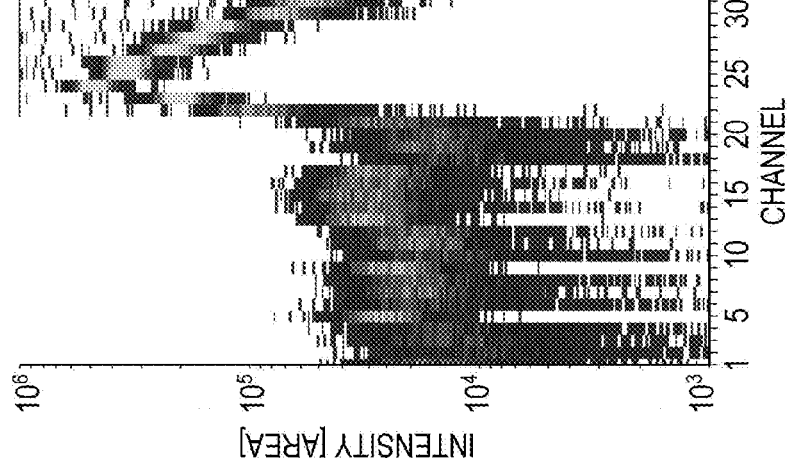

FINE PARTICLE MEASURING APPARATUS

CROSS REFERENCES TO RELATED APPLICATIONS

The present application is a continuation of U.S. application Ser. No. 14/289,214, filed May 28, 2014, which is a continuation of U.S. application Ser. No. 13/605,256, filed Sep. 6, 2012, which claims priority to Japanese Priority Patent Application JP 2011-199892 filed in the Japan Patent Office on Sep. 13, 2011, the entire content of which is hereby incorporated by reference.

BACKGROUND

The present application relates to a fine particle measuring apparatus which optically measures a property of a fine particle such as a cell.

A flow cytometer is an apparatus which irradiates fine particles such as cells and beads which flow in a flow cell with light and detects fluorescence or scattering light emitted from the fine particles so as to optically measure a property of each of the fine particles.

In a case of detecting fluorescence of a cell, for example, cells which are marked by fluorescence coloring matters are irradiated with excitation light such as laser light which has appropriate wavelength and intensity. Then, fluorescence emitted from the fluorescence coloring matters is condensed by a lens or the like and light in an appropriate wavelength band is selected with a wavelength selecting element such as a filter and a dichroic mirror so as to detect the selected light with a light-receiving element such as a photo multiplier tube (PMT). At this time, fluorescence from a plurality of fluorescence coloring matters marked on cells can be simultaneously detected and analyzed by combining a plurality of wavelength selecting elements and light-receiving elements. Further, the number of fluorescence coloring matters which can be analyzed can be increased by combining excitation light of a plurality of wavelengths.

As a method for detecting fluorescence with a flow cytometer, there is a method for measuring intensities of light beams in continuous wavelength bands as a fluorescence spectrum as well as the method in which a plurality of light beams in discontinuous wavelength bands are selected with a wavelength selecting element such as a filter so as to measure intensities of the light beams in respective wavelength bands. A spectrum type flow cytometer which is capable of measuring a fluorescence spectrum divides fluorescence emitted from fine particles with a spectral element such as a prism and a grating. Then, the flow cytometer detects the divided fluorescence with a light-receiving element array in which a plurality of light-receiving elements of different detection wavelength bands are arranged. As the light-receiving element array, a PMT array or a photodiode array in which light-receiving elements which are PMTs or photodiodes are one-dimensionally arranged, or an array in which a plurality of independent detection channels such as two-dimensional light-receiving elements which are CCDs or CMOSs are arranged is used.

Japanese Unexamined Patent Application Publication No. 2003-83894 is an example of related art.

SUMMARY

A measurement value of a flow cytometer includes an error caused by various factors. As a correcting method of a measurement error, a method using a standard sample of which a fluorescence property is previously identified, for example, is generally used. In this method, a relationship between an output value of current or the like and a fluorescence intensity (calibration information) about each light-receiving element is acquired based on a reference value obtained by measuring a plurality of standard samples and calibration is performed based on this relationship to obtain a measurement value.

In the above-described correcting method, a standard sample has to be measured in every measurement by a flow cytometer so as to acquire calibration information corresponding to an output of laser light and a setting value of a light-receiving element (for example, a voltage or the like in a case of a PMT). Thus, the above-described method is very complicated.

It is desirable to provide a fine particle measuring apparatus which can correct a measurement error by simple processing.

According to an embodiment, a fine particle measuring apparatus is provided that includes a detection unit configured to detect light emitted from a fine particle, and a processing unit having a memory device storing instructions which when executed by the processing unit, cause the processing unit to (a) calculate a corrected intensity value of the detected light; and (b) generate spectrum data based on the corrected intensity value.

By correcting an intensity value, which may be obtained in each of a plurality of light-receiving elements by a detection wavelength width of a corresponding light-receiving element, a measurement error caused by nonlinearity of an optical system of the apparatus can be compensated.

This fine particle measuring apparatus may be a spectrum type fine particle measuring apparatus which includes a spectral element configured to divide light from the fine particle and a light-receiving element array in which a plurality of light-receiving elements of different detection wavelength bands are arranged, as the detection unit. Especially, the fine particle measuring apparatus may be a spectrum type flow cytometer.

In this fine particle measuring apparatus, it is preferable that the processing unit correct the first corrected intensity value by using sensitivity data of each of the light-receiving elements so as to calculate a second corrected intensity value. By correcting the first corrected value by a relative sensitivity of each of the light-receiving elements, a measurement error caused by sensitivity difference among the light-receiving elements can be compensated.

Further, the processing unit may form a spectrum chart in which an axis expresses the detection wavelength and another axis expresses the first corrected intensity value or the second corrected intensity value, so as to output the spectrum chart to a display unit. Furthermore, it is preferable that the processing unit generate spectrum data using the detection wavelength as a parameter and the first corrected intensity value or the second corrected intensity value as another parameter, and compare the spectrum data with reference spectrum data that is stored in a storage unit, so as to output whether the both data are accorded with each other or are not accorded with each other to the display unit.

In the embodiment of the present application, "fine particles" widely include physiologically-related fine particles such as cells, microorganisms, and liposome, synthetic particles such as latex particles, gel particles, and industrial particles, and the like.

The physiologically-related fine particles include a chromosome, liposome, a mitochondrion, organelle, and the like which constitute various cells. Cells include animal cells (blood cells and the like) and plant cells. Microorganisms include bacterium such as a coli bacterium, viruses such as a tobacco mosaic virus, fungi such as a yeast cell, and the like. The physiologically-related fine particles may also include a physiologically-related polymer such as nucleic acid, protein, and a complex of nucleic acid and protein. Industrial particles may be organic polymeric materials, inorganic polymeric materials, metallic materials, or the like. Organic polymeric materials include polystyrene, styrene-divinylbenzen, polymethyl methacrylate, and the like. Inorganic polymeric materials include glass, silica, magnetic materials, and the like. Metallic materials include gold colloid, aluminum, and the like. These fine particles commonly have a spherical shape but may have a non-spherical shape. In addition, a size, mass, and the like of these fine particles are not especially limited.

According to the embodiment of the present application, a fine particle measuring apparatus which can correct a measurement error without measuring a standard sample in each sample analysis and can obtain an accurate analysis result is provided.

Additional features and advantages are described herein, and will be apparent from the following Detailed Description and the figures.

BRIEF DESCRIPTION OF THE FIGURES

FIGS. 8A to 8C are graphs illustrating spectrum charts of fluorescence beads FPK505 obtained by measurement with the flow cytometer which is experimentally produced in the embodiment, in which FIG. 8A illustrates a chart before the correction processing, FIG. 8B illustrates a chart based on a first corrected intensity value, and FIG. 8C illustrates a chart based on a second corrected intensity value;

FIGS. 9A to 9C are graphs illustrating spectrum charts of fluorescence beads FPK505 obtained by measurement with the flow cytometer which is experimentally produced in the embodiment, in which FIG. 9A illustrates a chart before the correction processing, FIG. 9B illustrates a chart based on a first corrected intensity value, and FIG. 9C illustrates a chart based on a second corrected intensity value;

FIGS. 10A to 10C are graphs illustrating spectrum charts of fluorescence beads FPK528 obtained by measurement with the flow cytometer which is experimentally produced in the embodiment, in which FIG. 10A illustrates a chart before the correction processing, FIG. 10B illustrates a chart based on a first corrected intensity value, and FIG. 10C illustrates a chart based on a second corrected intensity value;

FIGS. 11A to 11C are graphs illustrating spectrum charts of fluorescence beads FPK549 obtained by measurement with the flow cytometer which is experimentally produced in the embodiment, in which FIG. 11A illustrates a chart before the correction processing, FIG. 11B illustrates a chart based on a first corrected intensity value, and FIG. 11C illustrates a chart based on a second corrected intensity value; and FIGS. 12A to 12C are graphs illustrating spectrum charts of fluorescence beads FPK667 obtained by measurement with the flow cytometer which is experimentally produced in the embodiment, in which FIG. 12A illustrates a chart before the correction processing, FIG. 12B illustrates a chart based on a first corrected intensity value, and FIG. 12C illustrates a chart based on a second corrected intensity value.

DETAILED DESCRIPTION

Preferred embodiments of the present application will be described below in reference to the accompanying drawings. It should be noted that embodiments described below are merely an example of a typical embodiment of the present application and the scope of the present application is not interpreted limitedly by this example. The description will be given in the following order.

Figure 1:
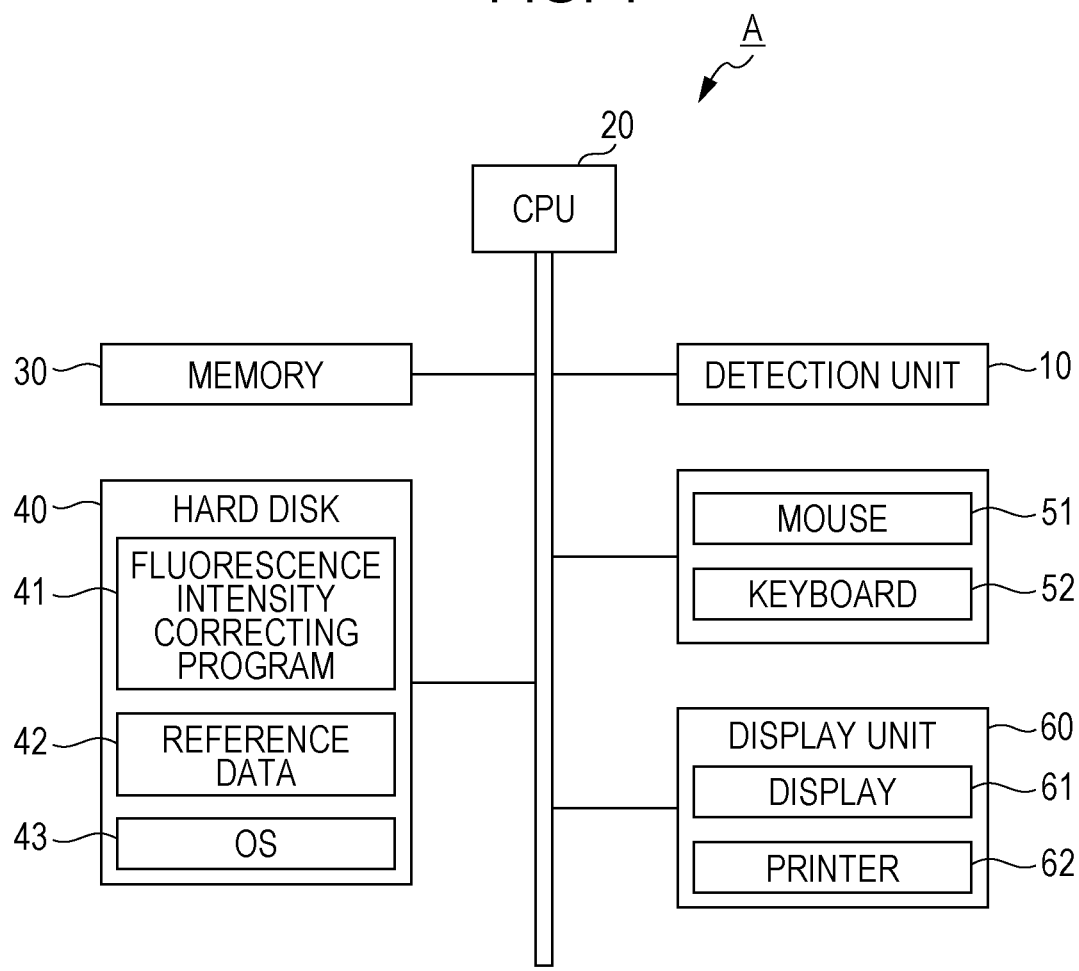
FIG. 1 is a block diagram illustrating the functional configuration of a fine particle measuring apparatus according to an embodiment of the present application.
Figure 2:
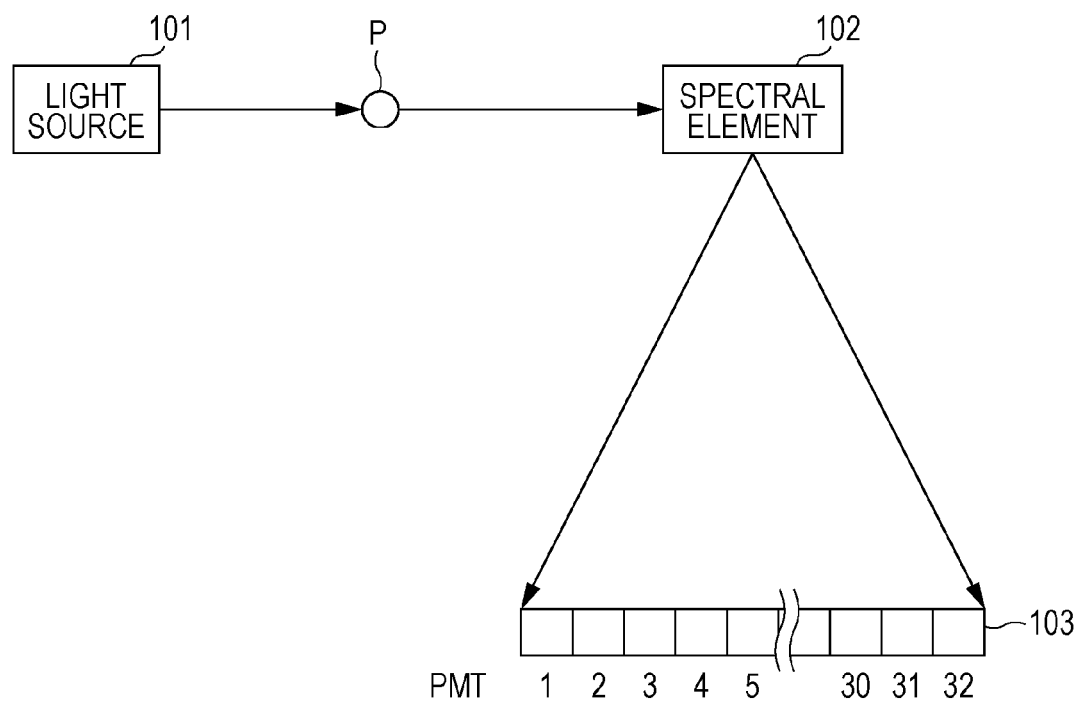
FIG. 2 is a schematic diagram illustrating the configuration of a detection unit of the fine particle measuring apparatus.

1. Fine Particle Measuring Apparatus According to An Embodiment
   (1) Configuration of Apparatus
   (2) Correction Processing of Fluorescence Intensity
      [Calculation of First Corrected Intensity Value]
      [Calculation of Second Corrected Intensity Value]
   (3) Data Display
   (4) Data Analysis
2. Fine Particle Measuring Apparatus According to Another Embodiment
   (1) Configuration of Apparatus
   (2) Correction Processing of Fluorescence Intensity
      [Calculation of First Corrected Intensity Value]
      [Calculation of Second Corrected Intensity Value]
   (3) Data Display 1. Fine Particle Measuring Apparatus According to an Embodiment (1) Configuration of Apparatus FIG. 1 is a block diagram illustrating the functional configuration of a fine particle measuring apparatus A according to an embodiment of the present application. FIG. 2 schematically illustrates the configuration of a detection unit 10 of the fine particle measuring apparatus A.

The fine particle measuring apparatus A includes the detection unit 10 which detects fluorescence emitted from fine particles by irradiating the fine particles with laser light and converts the intensity of the detected fluorescence into an electric signal to output the electric signal, a CPU 20, a memory 30, and a hard disk (storage unit) 40. In the fine particle measuring apparatus A, the CPU 20, the memory 30, and the hard disk (storage unit) 40 constitute a processing unit. The fine particle measuring apparatus A further includes a mouse 51, a keyboard 52, and a display unit 60 which is composed of a display 61 and a printer 62, as a user interface.

The detection unit 10 may have the configuration similar to that of a related art fine particle measuring apparatus. In particular, the detection unit 10 is composed of an irradiation system which condenses laser light from a light source 101 and irradiates fine particles P with the laser light and a detection system which includes a spectral element 102 which divides fluorescence emitted from fine particles P and a light-receiving element array 103 which detects the divided light. In the fine particle measuring apparatus A, fine particles P flow inside a flow path, which is formed in a flow cell or a microchip, in a manner to be arranged in a line.

The irradiation system includes a condenser lens for condensing laser light and irradiating fine particles P with the laser light, a dichroic mirror, a band pass filter, and the like (not depicted), other than the light source 101. Here, the light source 101 may be a light source obtained by combining two or more light sources which emit light beams having different wavelengths from each other. In this case, spots of fine particles P which are irradiated with two or more types of laser light may be same as each other or different from each other. Further, the detection system may include a condenser lens (not depicted) which condenses fluorescence emitted from fine particles P and introduces the fluorescence to the spectral element 102, for example. In this example, the configuration which employs a photo multiplier tube (PMT) array in which PMTs of 32 channels of different detection wavelength bands are one-dimensionally arranged is described as the light-receiving element array 103. Here, as the light-receiving element array 103, a photodiode array or an array in which a plurality of independent detection channels of different detection wavelength bands such as two-dimensional light-receiving elements which are CCDs or CMOSs are arranged may be employed.

In the fine particle measuring apparatus A, the detection unit 10 may be configured to detect not only fluorescence but also light which is emitted from fine particles P by irradiation of laser light, i.e. scattering light such as forward-scattering light, side-scattering light, Rayleigh scattering, and Mie scattering, and the like. Moreover, it should be reasonably understood that the light-receiving element array 103 may detect the frequency range of the divided light.

(2) Correction Processing of Fluorescence Intensity

The CPU 20 and the memory 30 perform correction processing of an intensity value of fluorescence based on an electric signal outputted form the detection unit 10 in collaboration with a fluorescence intensity correcting program 41 and an OS 43 which are stored in the hard disk 40. This correction processing includes a process of correcting an intensity value of fluorescence by a detection wavelength bandwidth of each light-receiving element (in this example, PMTs of channels 1 to 32) so as to calculate a first corrected intensity value and a process of correcting the first corrected intensity value by using sensitive data of each PMT so as to calculate a second corrected intensity value. It is also reasonably contemplated that the corrected intensity value may be based on a frequency range as an alternative to the wavelength bandwidth due to the inversely proportional relationship between frequency and the wavelength of light.

[Calculation of First Corrected Intensity Value]

Calculation of a first corrected intensity value is performed by dividing an intensity value of fluorescence acquired in each PMT by a detection wavelength bandwidth of a corresponding PMT.

In particular, the n-th intensity value obtained at a PMT of channel k among PMTs of channels 1 to 32 is denoted as I[k,n], a detection lower limit wavelength of the PMT of the channel k is denoted as L[k], and a detection upper limit wavelength is denoted as H[k]. In this case, a first corrected intensity value $J_1[k,n]$ is calculated by the following expression. Here, k denotes an integer from 1 to 32.

$$J_1[k,n]=I[k,n]/(H[k]-L[k])$$

When the optical system of the detection unit 10 including the spectral element 102 has nonlinearity, wavelength bandwidths of light beams which are detected at PMTs of the channels 1 to 32 are different from each other among the PMTs (refer to FIG. 5 described later). Therefore, intensity values of fluorescence acquired in the respective PMTs are relatively large in channels of which detection wavelength width is large and are relatively small in channels of which detection wavelength width is small, causing a measurement error.

Especially, in a case where fluorescence divided by the spectral element 102 is detected with the light-receiving element array 103 so as to measure a fluorescence spectrum of fine particles P, distortion of the spectrum shape is caused by the above-described measurement error in the fluorescence spectrum in which intensity values of fluorescence acquired in respective PMTs are directly used. That is, when a two-dimensional graph (referred to below as a "spectrum chart") of which the horizontal axis expresses a channel number and a vertical axis expresses an intensity value is compared to a spectrum chart of which a horizontal axis expresses a detection wavelength and a vertical axis expresses an intensity value, the intensity value is relatively larger in channels of which a detection wavelength width is larger, in the former chart. Therefore, fluorescence spectrum shapes of the both charts do not accord with each other. Thus, there is a gap between the fluorescence spectrum shapes.

With the first corrected intensity value which is obtained by dividing an intensity value of fluorescence acquired in each PMT by a detection wavelength bandwidth of a corresponding PMT, a measurement error caused by such nonlinearity of an optical system can be compensated.

The detection wavelength widths (H[k]–L[k]) of the respective PMTs are uniquely determined depending on a type and an arrangement of optical elements such as the spectral element 102, a condenser lens, a dichroic mirror, and a bandpass filter, which constitute the detection unit 10 (refer to FIG. 5 described later). Accordingly, if detection wavelength widths of respective PMTs are acquired at a stage on which apparatus design including selection and arrangement of optical elements is completed, a first corrected intensity value can be calculated based on an intensity value of fluorescence acquired at each of the PMTs.

[Calculation of Second Corrected Intensity Value]

Calculation of a second corrected intensity value is performed by dividing the first corrected intensity value acquired in each PMT by a relative sensitivity of a corresponding PMT.

In particular, a relative sensitivity of the PMT of the channel k among the PMTs of the channels 1 to 32 is denoted as S[k]. In this case, a second corrected intensity value $J_2[k,n]$ is calculated from the following expression.

$$J_2[k,n]=J_1[k,n]/S[k]$$

Here, the relative sensitivity is obtained such that an intensity value obtained in each channel by irradiating the PMT with light beams having the same intensities and wavelengths is expressed by a relative value with respect to an intensity value of a channel at which the largest intensity value is obtained. The relative sensitivity can be preliminarily calculated from sensitivity data in which electric signal amounts, which are outputted from respective channels when the PMTs are irradiated with light beams having the same intensities and wavelengths, are recorded. In this sensitivity data, sensitivity difference existing in respective PMTs and sensitivity difference (gain) which is set in respective PMTs by a user are both reflected. Here, the gain can be arbitrarily adjusted by changing a setting value such as an applied voltage by a user.

Sensitivities of the PMTs of the channels 1 to 32 are different among the PMTs due to individual difference of the PMTs and setting difference of the gain (refer to FIG. 6 described later). Therefore, the intensity values of fluorescence acquired in respective PMTs are relatively large in channels of which the sensitivity is high and are relatively small in channels of which the sensitivity is low, also causing a measurement error.

Especially, in a case where fluorescence divided by the spectral element 102 is detected with the light-receiving element array 103 so as to measure a fluorescence spectrum of fine particles P, distortion of the spectrum shape is caused by the above-described measurement error in the fluorescence spectrum in which intensity values of fluorescence acquired in respective PMTs are directly used. That is, the intensity value is relatively larger in a channel of which the sensitivity is higher, so that the shape of the fluorescence spectrum is distorted. Thus, the fluorescence spectrum is not accurate.

With the second corrected intensity value which is obtained by dividing the first corrected intensity value of each PMT by a relative sensitivity of a corresponding PMT, a measurement error caused by such sensitivity difference among light-receiving elements can be compensated.

(3) Data Display

The processing unit which includes the CPU 20, the memory 30, and the hard disk 40 forms a spectrum chart having a coordinate axis of the first corrected intensity value or the second corrected intensity value which is calculated, so as to output the spectrum chart to the display unit 60.

The spectrum chart may be formed such that the horizontal axis expresses a detection wavelength of each PMT and the vertical axis expresses the first corrected intensity value (refer to FIGS. 8B, 9B, 10B, 11B, and 12B described later). Further, the spectrum chart is preferably formed such that the horizontal axis expresses a detection wavelength and the vertical axis expresses the second corrected intensity value (refer to FIGS. 8C, 9C, 10C, 11C, and 12C described later).

In the spectrum chart, an intensity value may be expressed by a statistical number such as an average value, a standard error, a medium value, and a quartile point depending on the number of fine particles (number of events or density) which are detected based on a predetermined fluorescence intensity value in a predetermined detection wavelength (refer to FIGS. 9A to 9C described later). Further, the spectrum chart can be displayed as a three-dimensional graph to which a coordinate axis expressing the number of events is added and this three-dimensional graph can be pseudo-3D-displayed. Further, the spectrum chart can be multicolor-displayed by hue and saturation and/or lightness to which information (frequency information) about the number of fine particles (number of events or density) is reflected (refer to FIGS. 8A to 8C described later).

(4) Data Analysis

The processing unit which includes the CPU 20, the memory 30, and the hard disk 40 can generate spectrum data using the first corrected intensity value or the second corrected intensity value, which is calculated, as a first parameter and a detection wavelength of each PMT as a second parameter so as to execute various kinds of analysis by using the spectrum data. Here, the first parameter may be a statistical number such as an average value of first corrected intensity values or second corrected intensity values, a standard error, a medium value, and a quartile point, which are obtained by calculating all or part of a plurality of fine particles P which are measured.

Further, the processing unit can compare the generated spectrum data with reference spectrum data stored in the hard disk (storage unit) 40 so as to evaluate a degree of accordance between these pieces of data. Further, the processing unit can output the evaluation result to the display unit 60. Here, the reference spectrum data may be either spectrum data which is obtained such that fine particles including a previously-identified fluorescence substance are preliminarily measured by the fine particle measuring apparatus A and the above-described correction processing is performed, or spectrum data which is obtained by measuring a fluorescence spectrum of the fluorescence substance by a common spectrophotofluorometer. This is because a measurement value obtained by the fine particle measuring apparatus A can be directly compared to a measurement value obtained by a common spectrophotofluorometer due to correction. The reference spectrum data is stored in the hard disk 40 as reference data 42. As the evaluation method of the degree of accordance with the reference spectrum data, a sum of difference in respective detection wavelengths, a sum of absolute values of difference, or a square sum of difference, for example, can be used.

If the spectrum data which is obtained by measuring fine particles P by the fine particle measuring apparatus A and correcting the measurement result is compared with a piece or two or more pieces of reference spectrum data, whether fluorescence emitted from the measured fine particles P is similar to any of fluorescence recorded in the reference spectrum data can be determined. Accordingly, in a case where a kind of a fluorescence substance included in the measured fine particles P is unclear, for example, a fluorescence substance having high degree of similarity can be searched from the recorded reference spectrum data so as to predict a kind of a fluorescence substance included in the fine particles P.

Further, if the spectrum data which is obtained by measuring fine particles P by the fine particle measuring apparatus A and correcting the measurement result is compared with reference spectrum data which is preliminarily obtained by measuring the same fine particles P, the state of the fine particle measuring apparatus A can be evaluated. That is, there is a case where the state of the fine particle measuring apparatus A is deteriorated due to an effect of operation abnormality of the light-receiving element array, turbulence of flow of fine particles in a flow cell or a microchip, a gap due to temperature change or vibration of each element such as a lens and a spectral element, and the like and therefore, accuracy of measurement is degraded. It can be considered that measuring identical samples by the fine particle measuring apparatus A and the spectrophotofluorometer and comparing the results to check such apparatus state is an effective way. According to the embodiment of the present application, a measurement result obtained by the fine particle measuring apparatus A can be directly compared to a measurement result of the spectrophotofluorometer, so that the state can be simply and accurately evaluated.

In addition, if compensation processing using a plurality of pieces of reference spectrum data is performed with respect to spectrum data which is obtained by measuring fine particles P by the fine particle measuring apparatus A and correcting the measurement result, quantity of a plurality of fluorescence coloring matters included in fine particles P can be determined. For example, when fine particles P are dyed by a plurality of coloring matters $\{D_1, D_2, \ldots, D_n\}$, it is preferable that fluorescence coloring matters obtained from samples which are singly dyed by respective fluorescence coloring matters $\{D_1, D_2, \ldots, D_n\}$ be included in reference spectrum data used in the compensation processing. As the method of the compensation processing, a least-square method may be employed, for example.

2. Fine Particle Measuring Apparatus According to Another Embodiment

(1) Configuration of Apparatus

Figure 3:
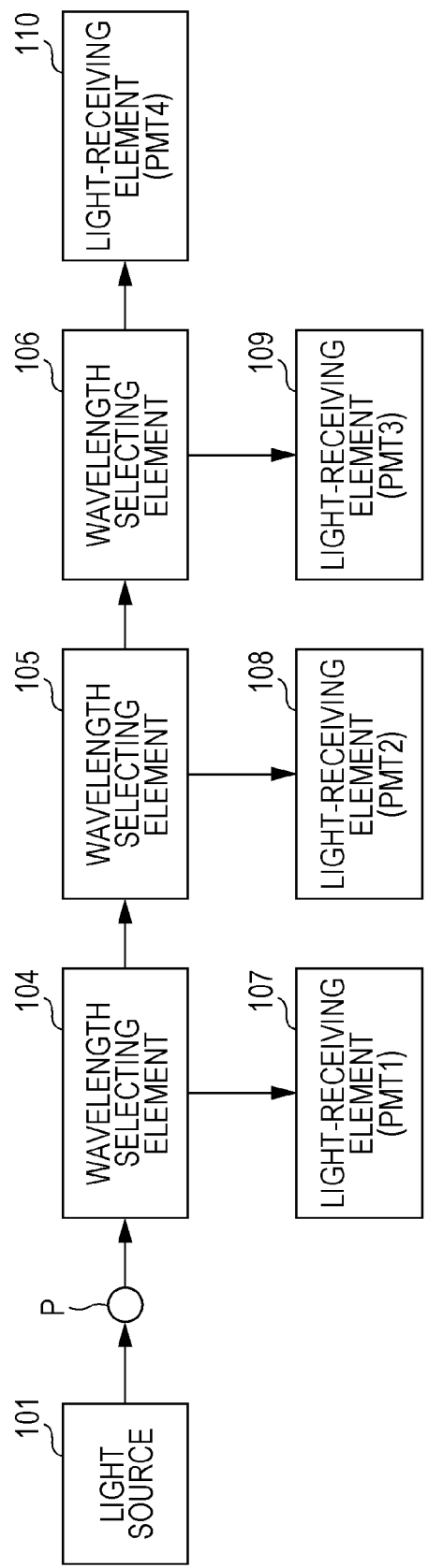
FIG. 3 is a schematic diagram illustrating the configuration of a detection unit of a fine particle measuring apparatus according to another embodiment of the present application.

FIG. 3 schematically illustrates the configuration of a detection unit 10 of a fine particle measuring apparatus B according to another embodiment of the present application. The functional configuration of the fine particle measuring apparatus B is same as that of the fine particle measuring apparatus A, which is depicted in FIG. 1, according to the embodiment described above, so that the description thereof is skipped.

The fine particle measuring apparatus B is different from the fine particle measuring apparatus A which measures intensities of light beams in continuous wavelength bands as a fluorescence spectrum, on the point that the fine particle measuring apparatus B selects a plurality of light beams in discontinuous wavelength bands by using a wavelength selecting element such as a filter and measures intensities of the light beams of respective wavelength bands.

The detection unit 10 of the fine particle measuring apparatus B is composed of an irradiation system which condenses laser light from a light source 101 and irradiates fine particles P with the laser light and a detection system which includes wavelength selecting elements 104 to 106 which select light in a predetermined wavelength band from fluorescence emitted from fine particles P and light-receiving elements 107 to 110 which detect the selected light. In the fine particle measuring apparatus B, fine particles P flow inside a flow path, which is formed in a flow cell or a microchip, in a manner to be arranged in a line.

The irradiation system includes a condenser lens for condensing laser light and irradiating fine particles P with the laser light, a dichroic mirror, a band pass filter, and the like (not depicted), other than the light source 101. Here, the light source 101 may be a light source obtained by combining two or more light sources which emit light beams having different wavelengths from each other. In this case, spots of fine particles P which are irradiated with two or more types of laser light may be same as each other or different from each other. Further, the detection system may include a condenser lens (not depicted) which condenses fluorescence emitted from fine particles P and introduces the fluorescence to the wavelength selecting element 104, for example. In this example, the configuration which employs photo multiplier tubes (PMTs) of different detection wavelength bands as the light-receiving elements 107 to 110 is described. Hereinafter, the channel numbers of the light-receiving elements 107 to 110 are respectively 1 to 4. Here, as the light-receiving elements 107 to 110, photodiodes may be used.

In the fine particle measuring apparatus B, the detection unit 10 can be configured to detect scattering light and the like as well as fluorescence, as is the case with the fine particle measuring apparatus A.

(2) Correction Processing of Fluorescence Intensity

The fine particle measuring apparatus B performs correction processing of an intensity value of fluorescence based on an electric signal outputted from the detection unit 10. This correction processing includes a process of correcting an intensity value of fluorescence by a detection wavelength bandwidth of each light-receiving element (in this example, PMTs of channels 1 to 4) so as to calculate a first corrected intensity value and a process of correcting the first corrected intensity value by using sensitive data of each PMT so as to calculate a second corrected intensity value.

[Calculation of First Corrected Intensity Value]

Calculation of a first corrected intensity value is performed by dividing an intensity value of fluorescence acquired in each PMT by a detection wavelength bandwidth of a corresponding PMT.

In particular, the n-th intensity value obtained at a PMT of channel k among PMTs of channels 1 to 4 is denoted as I[k,n], a detection lower limit wavelength of the PMT of the channel k is denoted as L[k], and a detection upper limit wavelength is denoted as H[k]. In this case, a first corrected intensity value $J_1[k,n]$ is calculated by the following expression. Here, k denotes an integer from 1 to 4.

$$J_1[k,n]=I[k,n]/(H[k]-L[k])$$

When the optical system of the detection unit 10 including the wavelength selecting elements 104 to 106 has nonlinearity, wavelength bandwidths of light beams which are detected at PMTs of the channels 1 to 4 are different from each other among the PMTs. Therefore, intensity values of fluorescence acquired in the respective PMTs are relatively large in channels of which detection wavelength width is large and are relatively small in channels of which detection wavelength width is small, causing a measurement error.

With the first corrected intensity value which is obtained by dividing an intensity value of fluorescence acquired in each PMT by a detection wavelength bandwidth of a corresponding PMT, a measurement error caused by such nonlinearity of an optical system can be compensated.

The detection wavelength widths (H[k]–L[k]) of the respective PMTs are uniquely determined depending on a type and an arrangement of optical elements such as the wavelength selecting elements 104 to 106, a condenser lens, a dichroic mirror, and a bandpass filter, which constitute the detection unit 10. Accordingly, if detection wavelength widths of respective PMTs are acquired at a stage on which apparatus design including selection and arrangement of optical elements is completed, a first corrected intensity value can be calculated based on an intensity value of fluorescence acquired at each of the PMTs.

[Calculation of Second Corrected Intensity Value]

Calculation of a second corrected intensity value is performed by dividing the first corrected intensity value acquired in each PMT by a relative sensitivity of a corresponding PMT.

In particular, a relative sensitivity of the PMT of the channel k among the PMTs of the channel 1 to 4 is denoted as S[k]. In this case, a second corrected intensity value $J_2[k,n]$ is calculated from the following expression.

$$J_2[k,n]=J_1[k,n]/S[k]$$

Sensitivities of the PMTs of the channels 1 to 4 are different among the PMTs due to individual difference of the PMTs and setting difference of the gain. Therefore, the intensity values of fluorescence acquired in respective PMTs are relatively large in channels of which the sensitivity is high and are relatively small in channels of which the sensitivity is low, also causing a measurement error.

With the second corrected intensity value which is obtained by dividing the first corrected intensity value of each PMT by a relative sensitivity of corresponding PMT, a measurement error caused by such sensitivity difference among light-receiving elements can be compensated.

(3) Data Display

The fine particle measuring apparatus B forms a two-dimensional graph having a coordinate axis of the first corrected intensity value or the second corrected intensity value which is calculated, and outputs the two-dimensional graph to the display unit 60.

Figure 4A:
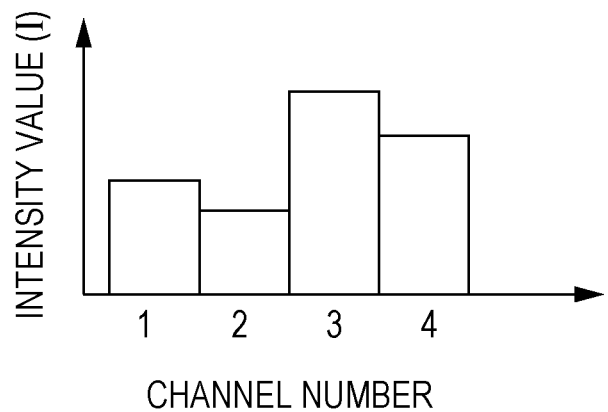
FIG. 4A is a graph illustrating an example of output data based on an intensity value before correction processing.
Figure 4B:
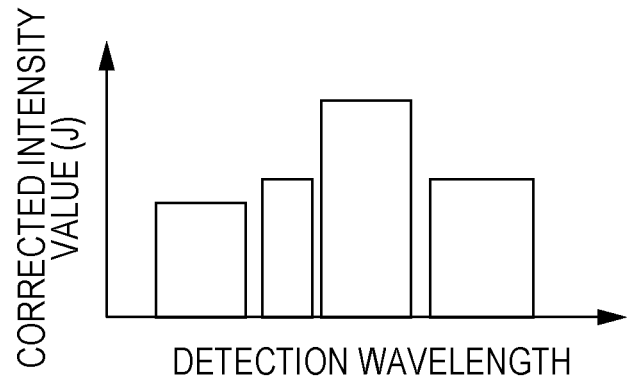
FIG. 4B is a graph illustrating an example of output data based on an intensity value after correction processing, with the fine particle measuring apparatus.

The two-dimensional graph may be formed such that the horizontal axis expresses a detection wavelength of each PMT and the vertical axis expresses the first corrected intensity value or the second corrected intensity value. FIG. 4A illustrates a graph before the correction processing, and FIG. 4B illustrates a graph based on the second corrected intensity value. FIG. 4A is a graph of which the horizontal axis expresses the channel number k (k is an integer from 1 to 4) and the vertical axis expresses a logarithm of an intensity value (I[k]) of fluorescence acquired in each channel. Further, FIG. 4B is a graph of which the horizontal axis expresses a detection wavelength and the vertical axis expresses a logarithm of a corrected value ($J_1[k]$ or $J_2[k]$) of a fluorescence intensity value acquired in each channel.

By the above-described correction processing, the fine particle measuring apparatus B can display a measurement result of intensities of light in discontinuous wavelength bands which are selected by using the wavelength selecting element, in a state that a measurement error caused by nonlinearity of the optical system of the apparatus and sensitivity difference among the light-receiving elements is compensated.

The fine particle measuring apparatus according to the embodiments of the present application may have the following configuration.

In an embodiment, a fine particle measuring apparatus includes a detection unit configured to detect light emitted from a fine particle, and a processing unit having a memory device storing instructions which when executed by the processing unit causes the processing unit to calculate a corrected intensity value of the detected light, and generate spectrum data based on the corrected intensity value.

In the fine particle measuring apparatus, the detection unit may be configured to generate an intensity value of the detected light.

In the fine particle measuring apparatus, the detection unit may include a plurality of light-receiving elements.

In the fine particle measuring apparatus, the processing unit may calculate the corrected intensity value based on a detection wavelength bandwidth of each of the plurality of light-receiving elements.

In the fine particle measuring apparatus, the processing unit may calculate the corrected intensity value based on a detection frequency range of each of the plurality of light-receiving elements.

In the fine particle measuring apparatus, the processing unit may calculate the corrected intensity value based on at least one of a detection wavelength bandwidth and a detection frequency range of each of the plurality of light-receiving elements.

In the fine particle measuring apparatus, the corrected intensity value may be a first corrected intensity value and the processing unit further calculates a second corrected intensity value based on the first corrected intensity value and relative sensitivity data of each corresponding one of the plurality of light-receiving elements.

In the fine particle measuring apparatus, the memory device storing instructions which when executed by the processor may cause the processor to compare the spectrum data with reference spectrum data.

The fine particle measuring apparatus may further include a display, and the memory device storing instructions which when executed by the processor causes the processor to display results of the comparison of spectrum data with the reference spectrum data.

In another embodiment, a device for receiving data from a detection unit is provided. The detection unit has a plurality of light-receiving elements configured to detect light emitted from a fine particle and convert the detected light to a corresponding intensity value. The device includes a processor and a memory device storing instructions which when executed by the processor, cause the processor to receive the intensity value of the detected light, correct the intensity value, and generate spectrum data based on the corrected intensity value.

In the device, the processor may correct the intensity value based on at least one of a detection wavelength bandwidth and a detection frequency range of each corresponding one of the plurality of light-receiving elements.

In the device, the memory device storing instructions which when executed by the processor may cause the processor to compare the spectrum data with reference spectrum data.

The device may further include a display, and the memory device storing instructions which when executed by the processor, cause the processor to display results of the comparison of spectrum data with the reference spectrum data.

In another embodiment, a device for receiving a corrected intensity value of detected light emitted from a fine particle includes a processor, and a memory device storing instructions which when executed by the processor, cause the processor to receive the corrected intensity value of the detected light, and generate spectrum data based on the corrected intensity value.

In the device, the memory device storing instructions which when executed by the processor, may cause the processor to compare the spectrum data with reference spectrum data.

The device may further include a display, and the memory device storing instructions which when executed by the processor, cause the processor to display results of the comparison of spectrum data with the reference spectrum data.

In another embodiment, a method for analyzing data includes detecting light emitted from a fine particle, correcting an intensity value of the detected light, and generating spectrum data based on the corrected intensity value.

In the method for analyzing data, the step of correcting the intensity value of detected light is may be based on at least one of a detection wavelength bandwidth and a detection frequency range corresponding to the detected light.

EXAMPLE

A spectrum type flow cytometer including the detection unit illustrated in FIG. 2 was produced experimentally. As a light source, a laser diode of the wavelength of 488 nm and a laser diode of the wavelength of 638 nm were used. Further, as a spectral element, a prism array obtained by combining a plurality of prisms was used. As a light-receiving element array, a PMT array of 32 channels was used and fluorescence of the wavelength from 500 nm to 800 nm was divide-detected.

Figure 5:
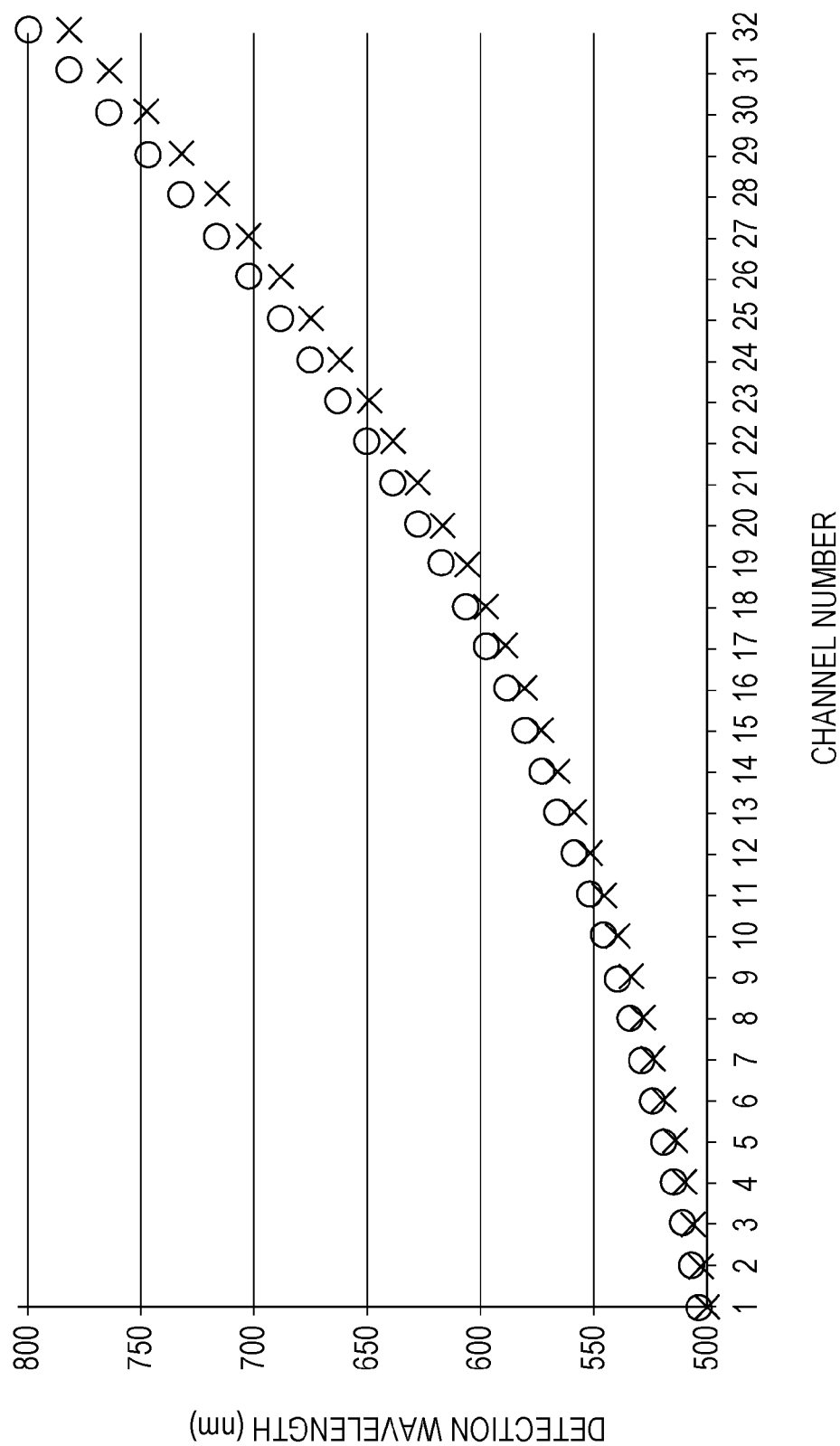
FIG. 5 is a graph illustrating a result that a detection wavelength of each PMT of a PMT array is determined by a flow cytometer which is experimentally produced in the embodiment.

FIG. 5 illustrates a graph of a result that detection wavelength bands of respective PMTs are determined in the trial apparatus. ">" in the graph denotes a detection lower limit wavelength (L[k]) of a PMT of each channel and "○" denotes a detection upper limit wavelength (H[k]). Here, k denotes an integer from 1 to 32. It can be confirmed that a detection wavelength bandwidth of a PMT in a long-wavelength side at which the channel number is large is larger among detection wavelength bandwidths (H[k]–L[k]) of respective PMTs. Here, in PMTs around the channel 21st which detect fluorescence of the wavelength around 638 nm, detected fluorescence is also restricted by an optical filter which prevents leak of laser light from a light source of the wavelength of 638 nm.

Figure 6:
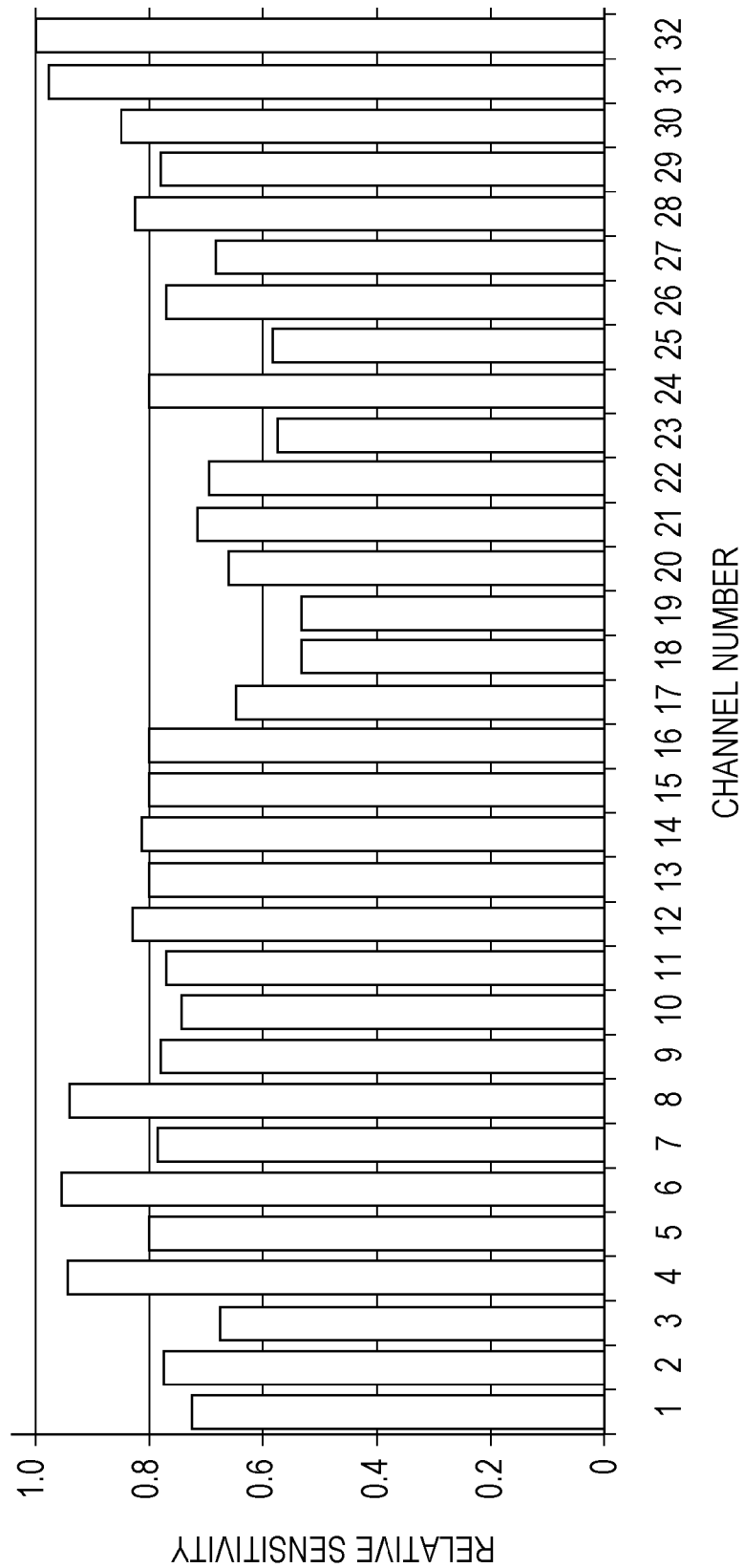
FIG. 6 is a graph illustrating a result that a relative sensitivity of each PMT of the PMT array is calculated by the flow cytometer which is experimentally produced in the embodiment.
Figure 7A:
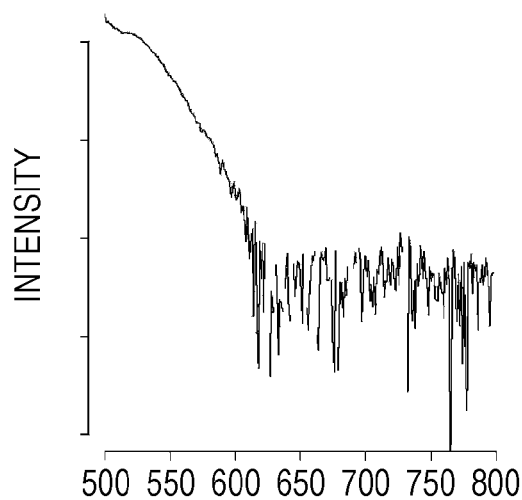
FIGS. 7A to 7D are graphs illustrating spectrum charts of fluorescence beads obtained by measurement with a spectrophotofluorometer in the embodiment.
Figure 7B:
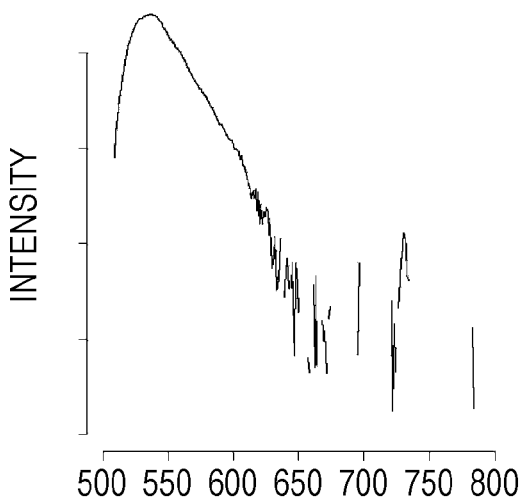
Figure 7C:
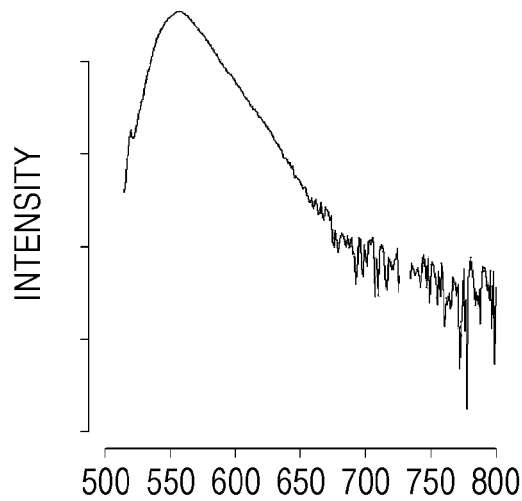
Figure 7D:
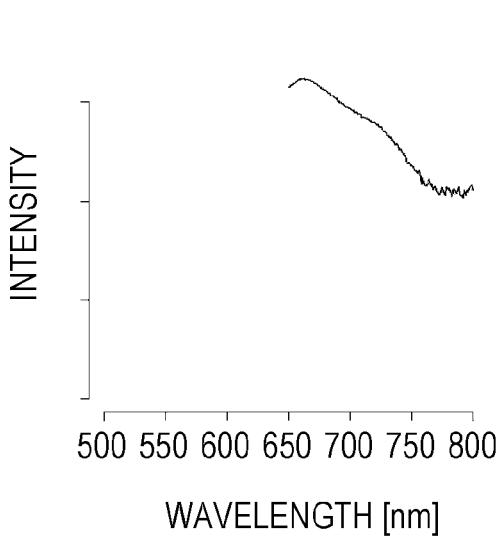

FIG. 6 illustrates a graph of calculation results of relative sensitivities of respective PMTs. The relative sensitivity is obtained such that intensity values which are obtained in respective channels by irradiating respective PMTs with light beams having the same intensities and wavelengths are expressed by relative values with respect to an intensity value of the channel 32, at which the strongest intensity value could be obtained, in a manner that the intensity value of the channel 32 is set to 1.

First, fluorescence spectrums of commercially-available fluorescence beads were measured by using an F-4500 type spectrophotofluorometer (Hitachi High-Technologies Corporation). As the fluorescence beads, four kinds of beads which were fluorescent particle kit (FPK) 505, FPK528, FPK549, and FPK667 obtained from Spherotech, Inc. were used. Obtained spectrum charts (reference spectrum charts) are illustrated in FIGS. 7A to 7D. FIG. 7A, FIG. 7B, FIG. 7C, and FIG. 7D respectively illustrate fluorescence spectrums of FPK505, FPK528, FPK549, and FPK667. The horizontal axes express a fluorescence wavelength (500 nm to 800 nm) and the vertical axes express a fluorescence intensity value (indicated in logarithm). Here, an excitation wavelength of the laser light is the wavelength of 488 nm in FIGS. 7A to 7C and is the wavelength of 638 nm in FIG. 7D.

Figure 10C:
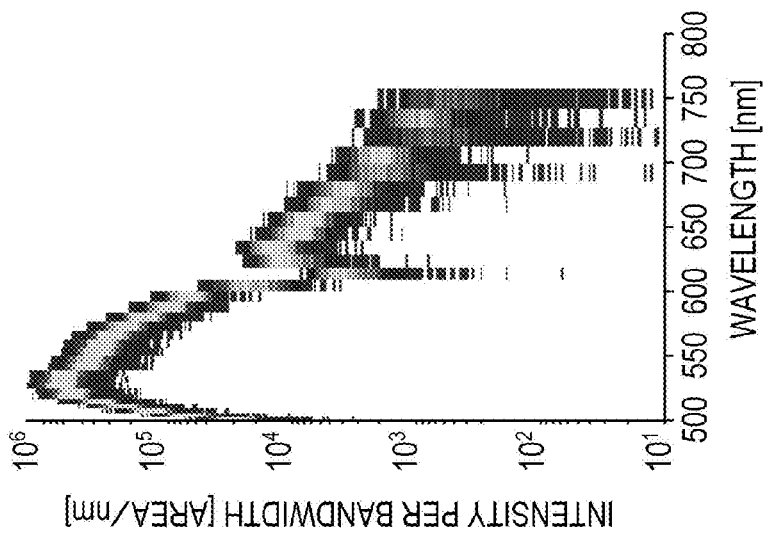
Figure 10B:
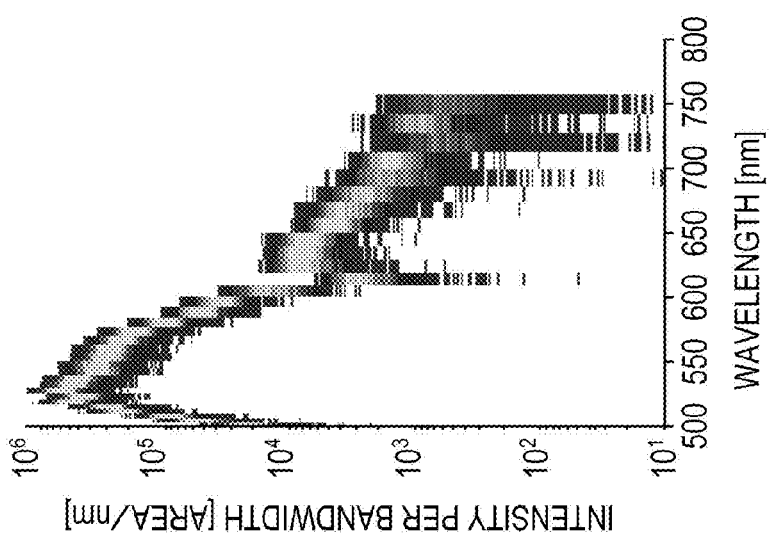
Figure 10A:
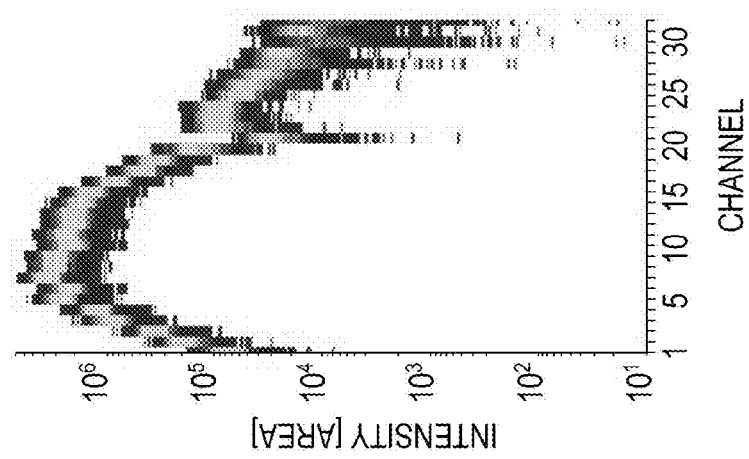
Figure 11A:
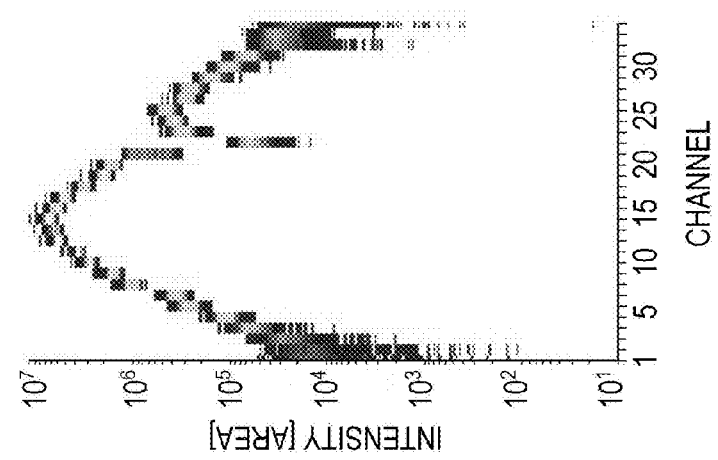
Figure 11B:
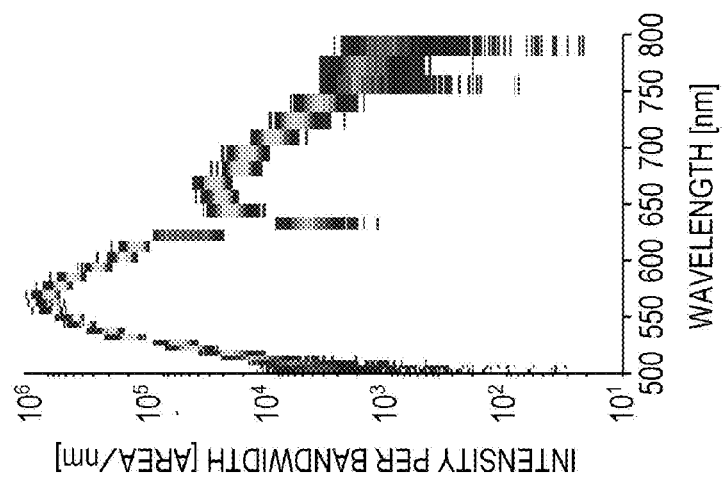
Figure 11C:
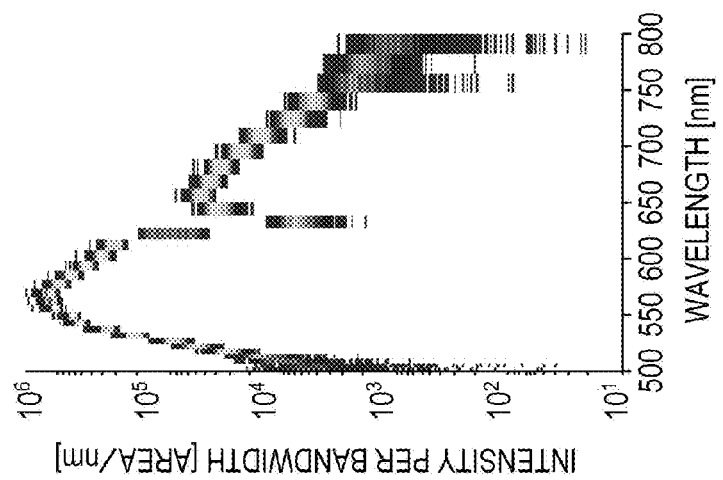

Fluorescence spectrums of the fluorescence beads were subsequently measured by using the trial apparatus. The obtained spectrum charts are illustrated in FIGS. 8A to 12C. FIGS. 8A to 9C illustrate charts of the FPK505, FIGS. 10A to 10C illustrate charts of the FPK528, FIGS. 11A to 11C illustrate charts of the FPK549, and FIGS. 12A to 12C illustrate charts of the FPK667. In FIGS. 8A to 8C, the number of events of respective channels is displayed by colors of the spectrums. Further, in FIGS. 9A to 9C, an intensity value is expressed by an average value (solid line) based on the number of events and an average value ±a standard deviation (dashed line).

FIGS. 8A, 9A, 10A, 11A, and 12A are spectrum charts of which the horizontal axis expresses the channel number and the vertical axis expresses a logarithm of an intensity value ($I[k]$, k denotes an integer from 1 to 32) of fluorescence obtained in each channel.

Spectrum shapes depicted in the spectrum charts of FIGS. 8A, 9A, 10A, 11A, and 12A are obviously different from spectrum shapes of the reference spectrum charts which are depicted in FIGS. 7A to 7D. This represents that the spectrum shape is distorted due to a measurement error caused by nonlinearity of an optical system of the apparatus and sensitivity difference among light-receiving elements, in a fluorescence spectrum obtained by directly using an intensity value ($I[k]$) of fluorescence obtained at a PMT.

FIGS. 8B, 9B, 10B, 11B, and 12B are spectrum charts of which the horizontal axis expresses a detection wavelength and the vertical axis expresses an logarithm of an first corrected value ($J_1[k]$, k denotes an integer from 1 to 32) of a fluorescence intensity value which is obtained in each channel. The first corrected intensity value $J_1[k]$ was obtained by dividing the intensity value ($I[k]$) of fluorescence obtained in each PMT by a detection wavelength bandwidth ($H[k]-L[k]$), which is depicted in FIG. 5, of a corresponding PMT. More specifically, the n-th intensity value $I[k,n]$ obtained at the PMT of the channel k was divided by a detection wavelength bandwidth ($H[k]-L[k]$) of the PMT to obtain the first corrected intensity value $J_1[k,n]$, and distribution of $J_1[k,n]$ was drawn in a range $L[k]$ to $H[k]$ of the horizontal axis so as to form a spectrum chart.

The spectrum shapes depicted in the spectrum charts of FIGS. 8B, 9B, 10B, 11B, and 12B are approximately accorded with the spectrum shapes of the reference spectrum charts of FIGS. 7A to 7D. This represents that a measurement error caused by nonlinearity of the optical system of the apparatus was compensated by the correction processing in which an intensity value ($I[k]$) of fluorescence obtained in each PMT was divided by a detection wavelength bandwidth ($H[k]-L[k]$) of a corresponding PMT, and distortion of the spectrum shapes could be corrected.

FIGS. 8C, 9C, 10C, 11C, and 12C are spectrum charts of which the horizontal axis expresses a detection wavelength and the vertical axis expresses an logarithm of an second corrected value ($J_2[k]$, k denotes an integer from 1 to 32) of a fluorescence intensity value which is obtained in each channel. The second corrected intensity value $J_2[k]$ was obtained by dividing the first corrected intensity value ($J_1[k]$) by a relative sensitivity ($S[k]$), which is depicted in FIG. 6, of a corresponding PMT.

Spectrum shapes depicted in spectrum charts of FIGS. 8C, 9C, 10C, 11C, and 12C are well accorded with spectrum shapes of the reference spectrum charts depicted in FIGS. 7A to 7D. Especially, though distortion of the spectrum shapes which seems to be caused by sensitive difference of PMTs is observed in a region of the wavelength of about 500 nm in the spectrum charts based on the first corrected value ($J_1[k]$) of FIGS. 8B, 9B, 10B, 11B, and 12B, this distortion is corrected in the spectrum charts based on the second corrected value ($J_2[k]$) of FIGS. 8C, 9C, 10C, 11C, and 12C. This has proved that a measurement error caused by sensitivity difference among light-receiving elements is compensated by the correction processing in which the first corrected value ($J_1[k]$) is divided by a relative sensitivity ($S[k]$) of a corresponding PMT and distortion of the spectrum shapes can be corrected.

According to the fine particle measuring apparatus of the embodiments of the present application, from the above-described results, it can be understood that a spectrum shape, which is well accorded with a reference spectrum chart which is obtained by measuring by a common spectrophotofluorometer, of fine particles can be measured.

Therefore, in the fine particle measuring apparatus according to the embodiments of the present application, a spectrum shape of a sample of which the type or the quantity of marking fluorescence coloring matters are not previously identified is detected from a database (reference data) in which a spectrum shape of fluorescence which is previously identified is recorded, being able to predict the type or the quantity of the fluorescence coloring matters marked on the sample.

Further, in the fine particle measuring apparatus according to the embodiments of the present application, compensation calculation performed when a sample marked by a plurality of fluorescence coloring matters is analyzed can be performed by using a fluorescence spectrum of each fluorescence coloring matter which is preliminarily measured without performing measurement, which has been performed in related art, of a sample which is singly dyed by each fluorescence coloring matter. Accordingly, work and time for sample analysis and resources of reagents and the like can be reduced.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An information processing apparatus comprising:
a processor; and
a memory device storing instructions which when executed by the processor, cause the processor to generate spectrum data based on intensity value corresponding to light from a sample detected by a plurality of light receiving elements,
wherein the spectrum data is generated based on a corrected intensity value calculated by using the intensity value and at least one of a detection wavelength bandwidth and a detection frequency range of each of the plurality of light receiving elements.

2. The information processing apparatus of claim 1, wherein the sample is a fine particle.

3. The information processing apparatus of claim 1, wherein the plurality of light receiving elements include different detection wavelength bands.

4. The information processing apparatus of claim 1, wherein the corrected intensity value includes a first corrected intensity value and the processor further calculates a second corrected intensity value based on the first corrected intensity value and relative sensitivity data of each corresponding one of the plurality of light receiving elements.

5. The information processing apparatus of claim 1, wherein the memory device storing instructions which when executed by the processor, cause the processor to compare the spectrum data with reference spectrum data.

6. The information processing apparatus of claim 1, wherein the processor is configured to form a spectrum chart in which an axis expresses a detection wavelength and another axis expresses the corrected intensity value, so as to output the spectrum chart to a display.

7. The information processing apparatus of claim 6, wherein the corrected intensity value in the spectrum chart is expressed by at least one of a statistical number including an average value, a standard error and a medium value, and a quartile point depending on a number of samples.

8. The information processing apparatus of claim 6, wherein the spectrum chart is configured to be displayed as a three dimensional graph.

9. An analyzing apparatus comprising:
a detection unit having a plurality of light receiving elements configured to detect light emitted from a sample;
a processor; and
a memory device storing instructions which when executed by the processor, cause the processor to generate spectrum data based on intensity value corresponding to the detected light,
wherein the spectrum data is generated based on a corrected intensity value calculated by using the intensity value and at least one of a detection wavelength bandwidth and a detection frequency range of each of the plurality of light receiving elements.

10. The analyzing apparatus of claim 9, wherein the sample is a fine particle.

11. The analyzing apparatus of claim 9, wherein the plurality of light receiving elements includes different detection wavelength bands.

12. The analyzing apparatus of claim 9, further comprising a display,
wherein the memory device storing instructions which when executed by the processor, cause the display to display a spectrum chart in which an axis expresses a detection wavelength and another axis expresses the corrected intensity value.

13. The analyzing apparatus of claim 12, wherein the corrected intensity value in the spectrum chart is expressed by at least one of a statistical number including an average value, a standard error and a medium value, and a quartile point depending on a number of samples.

14. The analyzing apparatus of claim 12, wherein the spectrum chart is configured to be displayed as a three dimensional graph.

15. The analyzing apparatus of claim 9, wherein the corrected intensity value is a first corrected intensity value and the process is configured to further calculate a second corrected intensity value based on the first corrected intensity value and relative sensitivity data of each corresponding one of the plurality of light receiving elements.

16. The analyzing apparatus of claim 9, wherein the memory device storing instructions which when executed by the processor, cause the processor to compare the spectrum data with reference spectrum data.

17. The analyzing apparatus of claim 16, further comprising a display,
wherein the memory device storing instructions which when executed by the processor, cause the processor to display results of the comparison of the spectrum data with the reference spectrum data.

* * * * *